United States Patent
Liu et al.

(10) Patent No.: US 11,733,137 B2
(45) Date of Patent: Aug. 22, 2023

(54) SLOPE ONE-WAY LOADING RUTTING TEST DEVICE FOR EVALUATING THE RESISTANCE TO HIGH TEMPERATURE DEFORMATION OF A RAMP ASPHALT MIXTURE

(71) Applicant: Tongji University, Shanghai (CN)

(72) Inventors: Liping Liu, Shanghai (CN); Lijun Sun, Shanghai (CN); Ning Liu, Shanghai (CN); Ruikang Yang, Shanghai (CN); Huailei Cheng, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 12 days.

(21) Appl. No.: 17/401,579

(22) Filed: Aug. 13, 2021

(65) Prior Publication Data
US 2022/0057310 A1 Feb. 24, 2022

(30) Foreign Application Priority Data
Aug. 18, 2020 (CN) .......................... 202010833355.4

(51) Int. Cl.
*G01N 3/10* (2006.01)
*G01N 3/06* (2006.01)
*G01N 33/42* (2006.01)

(52) U.S. Cl.
CPC .............. *G01N 3/10* (2013.01); *G01N 3/06* (2013.01); *G01N 33/42* (2013.01); *G01N 2203/0019* (2013.01); *G01N 2203/0037* (2013.01); *G01N 2203/0048* (2013.01); *G01N 2203/0058* (2013.01); *G01N 2203/0226* (2013.01); *G01N 2203/06* (2013.01); *G01N 2203/0682* (2013.01); *G01N 2203/0694* (2013.01)

(58) Field of Classification Search
CPC .. G01N 3/14; G01N 1/28; G01N 3/38; G01N 3/04; G01D 21/00; G01D 21/02; G01M 7/02; G01M 7/08; G01M 1/045; G01M 13/00; G01M 17/045; G01M 17/10; G01L 3/26; G01L 5/282; G01L 5/28; B60C 19/00; G09B 9/04
See application file for complete search history.

(56) References Cited

FOREIGN PATENT DOCUMENTS

CN 112067476 A * 12/2020 ............... G01N 3/02

* cited by examiner

*Primary Examiner* — Brandi N Hopkins
(74) *Attorney, Agent, or Firm* — Brian S. Boyer; Syndicated Law, PC.

(57) ABSTRACT

The invention discloses a slope one-way loading rutting test device, wherein the upper part of a loading frame is slidably connected with an upper cross beam of a frame through a loading frame rotating assembly, and a variable speed motor and a runner wheel are embedded in the lower part of the loading frame. The variable speed motor is in transmission connection with the runner wheel to realize one-way continuous loading of the runner wheel on a test piece. The lower part of a bearing frame is slidably connected with a lower cross beam of a frame through a bearing frame rotating assembly, a test piece mounting frame and a height adjusting device are sequentially embedded into the upper part of the bearing frame from top to bottom, and the height of the test piece mounting frame is adjusted through the height adjusting device.

6 Claims, 4 Drawing Sheets

SLOPE ONE-WAY LOADING RUTTING TEST DEVICE FOR EVALUATING THE RESISTANCE TO HIGH TEMPERATURE DEFORMATION OF A RAMP ASPHALT MIXTURE

CROSS REFERENCE TO RELATED APPLICATION(S)

This patent application claims the benefit and priority of Chinese Patent Application No. 202010833355.4, filed on Aug. 18, 2020, the disclosure of which is incorporated by reference herein in its entirety as part of the present application.

TECHNICAL FIELD

The present disclosure relates to the technical field of pavement material test devices, in particular to a slope one-way loading rutting test device, which is used for rutting test of ramp asphalt mixture.

BACKGROUND ART

As one of the main diseases of asphalt pavement, high-temperature rutting has an important impact on the service quality and service life of pavement. As the most ideal simulation test of road compaction, rutting test is often used to evaluate the high-temperature rutting resistance of asphalt pavement because its test piece structure is very similar to the road compaction layer.

At present, the indoor experimental methods used to evaluate the high-temperature rutting resistance of asphalt pavement mainly comprise: TEST CODE FOR ASPHALT AND ASPHALT MIXTURE IN HIGHWAY ENGINEERING JTG E20-2011 of Chinese standard rutting test, Hamburg rutting test, French rutting test, pavement analyzer rutting test and small accelerated loading rutting test, etc. However, the rutting tester used in the above methods has the following problems. 1. The runner wheel uses reciprocating linear running and loading; 2. During the test, the test piece is placed horizontally, and its loading surface is horizontal; 3. The running speed and contact pressure of the runner wheel are unique, which is seriously divorced from reality. From the above analysis, it can be known that the existing rutting instrument can only simulate the rutting damage of the horizontal sections of road under specific traffic flow.

At present, the traffic environment becomes more complicated due to the surge of traffic flow, complex terrain, changeable routes and the increase of heavy load and overload. From the simulation of road scenes, the existing rutting instrument has shortcomings in simulating the road surface slope, the wheel running mode, the wheel running speed and the contact pressure on traffic lanes, and cannot reflect the actual traffic situation. In view of the above-mentioned technical problems, relevant experts and scholars have also made some useful explorations. CN 109490063 B invents an annular rutting test chamber capable of setting temperature and humidity, and wheel load and simulating dynamic water washing. CN 207703656 U invents a rutting tester for evaluating the rutting resistance of asphalt mixture under different slope conditions. CN 207197965 U invents a rutting tester with one-way annular loading. CN 107063902 B invents a rutting instrument with a runner wheel loaded along an annular track and a rutting test method based on the test device. CN 105954113 A invents a rutting test device for asphalt mixture ring roads and a test method. CN 204188466 U invents a rutting tester capable of loading the test piece in the same direction. CN 101736680 B invents an asphalt mixture rutting tester continuously loading through multiple driving wheels. CN 101666727 B invents an indoor rutting test device for small-sized annular asphalt pavement. CN 201045608 Y invents a rutting tester which simulates asphalt mixture on heavy-duty ramps by horizontally placing test pieces, wherein the rutting tester can carry out one-way heavy-duty loading under the condition of immersion. CN 100543444 C invents an indoor rotary rutting tester, which uses multiple wheels to perform one-way annular rotation to load multiple groups of test pieces.

According to the analysis of the above patents, at present, some achievements have been made in the research on a single aspect such as one-way annular loading, continuous loading, slope loading and loading environment setting, but the above patents still have some defects in the research of simulating rutting damage on road surfaces of different slopes under different traffic flows (different speeds) when considering the uphill and downhill of the vehicle. Therefore, in order to meet the demands of engineering test detection and scientific research of tests, at present, there is an urgent need for a new asphalt mixture rutting tester, which can realize the oblique arrangement of test pieces, the one-way continuous loading of the runner wheel and the adjustable running speed and contact pressure of the runner wheel, so that the rutting damage on road surfaces of different slopes under different traffic flows (different speeds) can be simulated when considering the uphill and downhill of vehicles.

SUMMARY

Therefore, the present disclosure provides a slope one-way loading rutting test device, which solves the problems that an existing rutting tester cannot simulate rutting damage on road surfaces of different slopes when considering the uphill and downhill of vehicles, and simulation cannot truly reflect the actual effect of wheels on the road surface of a traffic lane.

In order to achieve the above purpose, the present disclosure provides the following technical scheme.

According to the present disclosure, a slope one-way loading rutting test device is provided, comprising a frame, a loading frame rotating assembly, a loading frame, a variable speed motor, a runner wheel, a bearing frame, a bearing frame rotating assembly, a height adjusting device, a test piece mounting frame and a temperature control box, wherein the upper part of the loading frame is slidably connected with an upper cross beam of the frame through the loading frame rotating assembly, and the variable speed motor and the runner wheel are embedded in the lower part of the loading frame; the variable speed motor is in transmission connection with the runner wheel to realize one-way continuous loading of the runner wheel on a test piece; the lower part of a bearing frame is slidably connected with a lower cross beam of the frame through a bearing frame rotating assembly, and the test piece mounting frame and the height adjusting device are sequentially embedded into the upper part of the bearing frame from top to bottom; the height of the test piece mounting frame is adjusted through the height adjusting device; the temperature control box wraps the frame in a closed mode and is used for regulating and controlling the test environment temperature.

Further, the slope one-way loading rutting test device further comprises a transmission chain, one end of the transmission chain is connected with the variable speed motor, the other end of the transmission chain is connected with the rotating mandrel of the runner wheel, the transmission chain serves as a transmission device for the variable speed motor driving the runner wheel to run and load, and the runner wheel is a pneumatic rubber tire.

Further, the rotating spindle of the variable speed motor is in transmission connection with the transmission chain, the variable speed motor drives the runner wheel to run and load through the transmission chain with adjustable rotating speed, and the variable speed motor is fixedly mounted on the bottom of the loading frame.

Further, the slope one-way loading rutting test device further comprises a temperature sensor and a displacement sensor, wherein the temperature sensor is used to measure the surface temperature of the test piece in the experimental process, and the displacement sensor is used to measure the vertical displacement of the surface of the test piece which changes with time under the action of the runner wheel in the experimental process.

Further, the frame has a rectangular door frame structure, the frame consists of left and right upright posts and upper and lower cross beams, and the frame mainly provides a stable working platform for test loading.

Further, the loading frame rotating assembly consists of upper and lower arc sliding plates, the shapes of the upper and lower arc sliding plates are semi-circular, the inner diameter of the semi-circular sliding plates is equal to the outer diameter of the semi-circular arc of the loading frame, and the two arcs are concentric.

Further, the shape of the loading frame is semi-cylindrical, and the loading frame rotating assembly is mounted on the top of the semi-circular arc of the loading frame.

Further, the shape of the bearing frame is semi-cylindrical, the bearing frame has the same radius and height as the semi-cylinder of the loading frame, the bearing frame rotating assembly is mounted on the top of the semi-circular arc of the bearing frame, and the mounting height of the bearing frame ensures that the semi-circular arc center of the loading frame coincides with the semi-circular arc center of the bearing frame, so as to ensure that the opposite faces of the loading frame and the bearing frame are always parallel faces when the loading frame and the bearing frame rotate at the same angle in the same direction.

Further, the bearing frame rotating assembly consists of upper and lower arc sliding plates, the shapes of the upper and lower arc sliding plates are semi-circular, the inner diameter of the semi-circular sliding plates is equal to the outer diameter of the semi-circular arc of the bearing frame, and the two arcs are concentric.

Further, the height adjusting device is a hydraulic height adjusting system, the height adjusting device adjusts the contact pressure of the runner wheel by adjusting the height of the test piece mounting frame, the height adjusting device is mounted between the test piece mounting frame and the bearing frame, the upper end of the height adjusting device is fixedly connected with the test piece mounting frame, and the lower end of the height adjusting device is fixedly connected with the bearing frame; the test piece mounting frame is a rectangular steel platform, the upper surface of the test piece mounting frame is provided with a test mold neck which plays a role of fixing a test mold, and the lower surface of the test piece mounting frame is seated and fixedly mounted right above the height adjusting device; the temperature control box has a rectangular box structure, and the temperature control box has the functions of heating up and preserving heat, and is used for regulating and controlling the temperature of the test environment.

Compared with the traditional asphalt mixture rutting tester, the slope one-way loading rutting tester provided by the present disclosure has the following beneficial effects. On the one hand, in terms of the test piece loading mode, the runner wheel adopts a pneumatic rubber wheel for one-way continuous loading, and the running speed and the contact pressure of the runner wheel are adjustable, which changes the fact that the existing rutting tester adopts solid rubber runner wheels for reciprocating cyclic loading and cannot truly simulate the actual effect of wheels on the road surface of a traffic lane. On the other hand, in the mounting position of the test piece, the oblique arrangement is adopted, and the inclination angle is adjustable, which changes the situation that the existing rutting tester can only load the test piece horizontally, but cannot simulate the rutting damage on road surfaces of different slopes (long and large longitudinal slopes) when considering the uphill and downhill of vehicles. On the whole, the slope one-way loading rutting test device can simulate the rutting damage on road surfaces of different slopes under different traffic flows when considering the uphill and downhill of vehicles, and the runner wheel adopts a pneumatic rubber wheel for one-way continuous loading, which is closer to the actual effect of wheels on the road surface of a traffic lane. In the design, considering the actual effect of the real wheels on the road surface of a traffic lane and the prevailing reality of the longitudinal slope of the road surface, the test piece is obliquely arranged with the angle is adjustable, the runner wheel adopts an pneumatic rubber wheel for one-way continuous loading, and the running speed and the contact pressure of the runner wheel are adjustable, so that the problems that an existing rutting tester cannot simulate rutting damage on road surfaces of different slopes under different traffic flows when considering the uphill and downhill of vehicles, and simulation cannot truly reflect the actual effect of wheels on the road surface of a traffic lane are effectively solved.

BRIEF DESCRIPTION OF THE DRAWINGS

In order to explain the embodiment of the present disclosure or the technical scheme in the prior art more clearly, the drawings used in the description of the embodiment or the prior art will be briefly introduced hereinafter. Obviously, the drawings in the following description are only exemplary. For those skilled in the art, other implementation drawings can be obtained from the provided drawings without paying creative labor.

The structure, scale, size, etc. shown in this specification are only used to match the contents disclosed in this specification for those skilled in the art to understand and read, rather than limit the limiting conditions implemented by the present disclosure. Therefore, it has no technical substantive significance. Any modification of structure, change of scale relationship or adjustment of size should still fall within the scope covered by the technical contents disclosed in the present disclosure without affecting the effects and goals achieved by the present disclosure.

In the figures: 1. Frame, 2. Loading frame, 3. Loading frame rotating assembly, 4. Variable speed motor, 5. Transmission chain, 6. Runner wheel, 7. Bearing frame, 8. Bearing frame rotating assembly, 9. Height adjusting device, 10. Test piece mounting frame, 11. Temperature control box, 12. Temperature sensor, 13. Displacement sensor.

DETAILED DESCRIPTION OF THE EMBODIMENTS

The embodiments of the present disclosure will be explained by specific embodiments hereinafter. Those skilled in the art can easily understand other advantages and effects of the present disclosure from the contents disclosed in this specification. Obviously, the described embodiments are some embodiments of the present disclosure, rather than all of the embodiments. Based on the embodiments of the present disclosure, all other embodiments obtained by those skilled in the art without paying creative labor belong to the scope of protection of the present disclosure.

Embodiment 1

Figure 1:
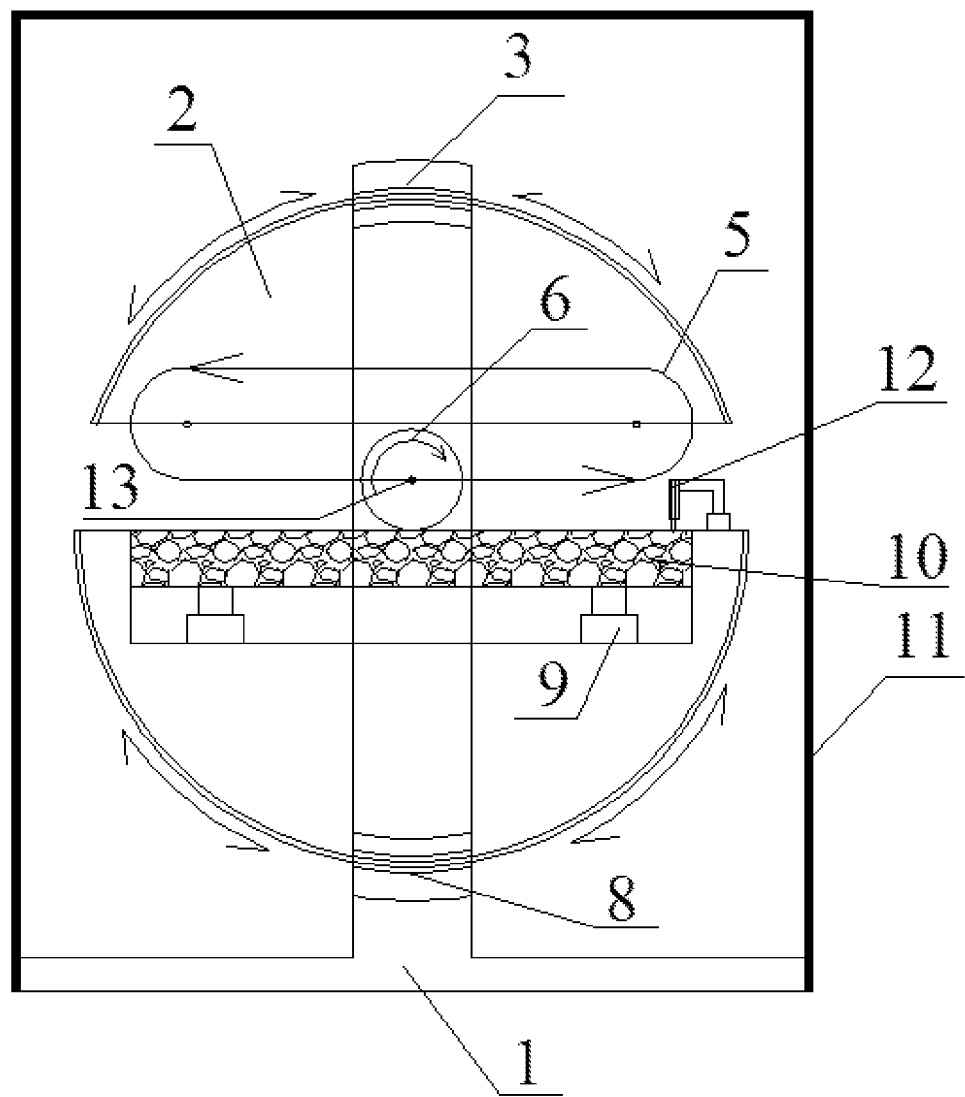
FIG. 1 is a front view of a slope one-way loading rutting test device according to some embodiments of the present disclosure when simulating plane loading.
Figure 2:
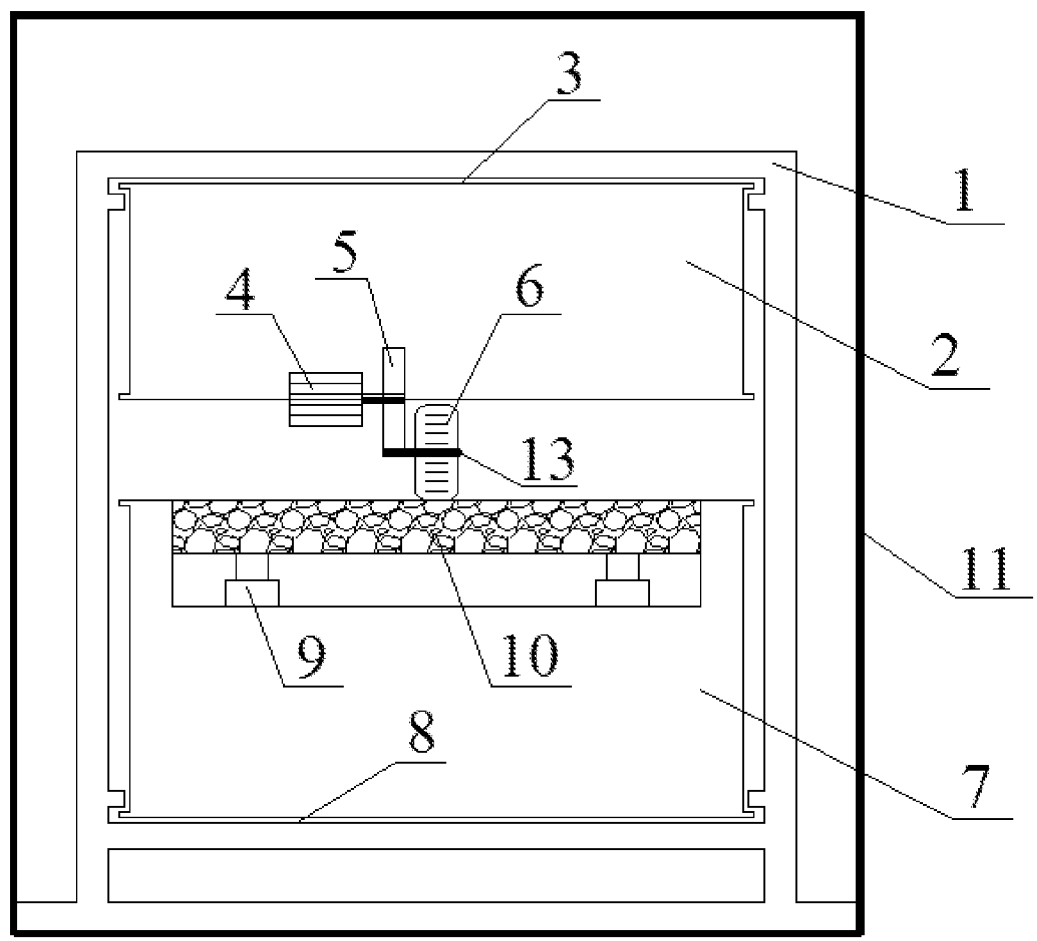
FIG. 2 is a side view of a slope one-way loading rutting test device according to some embodiments of the present disclosure when simulating plane loading.
Figure 3:
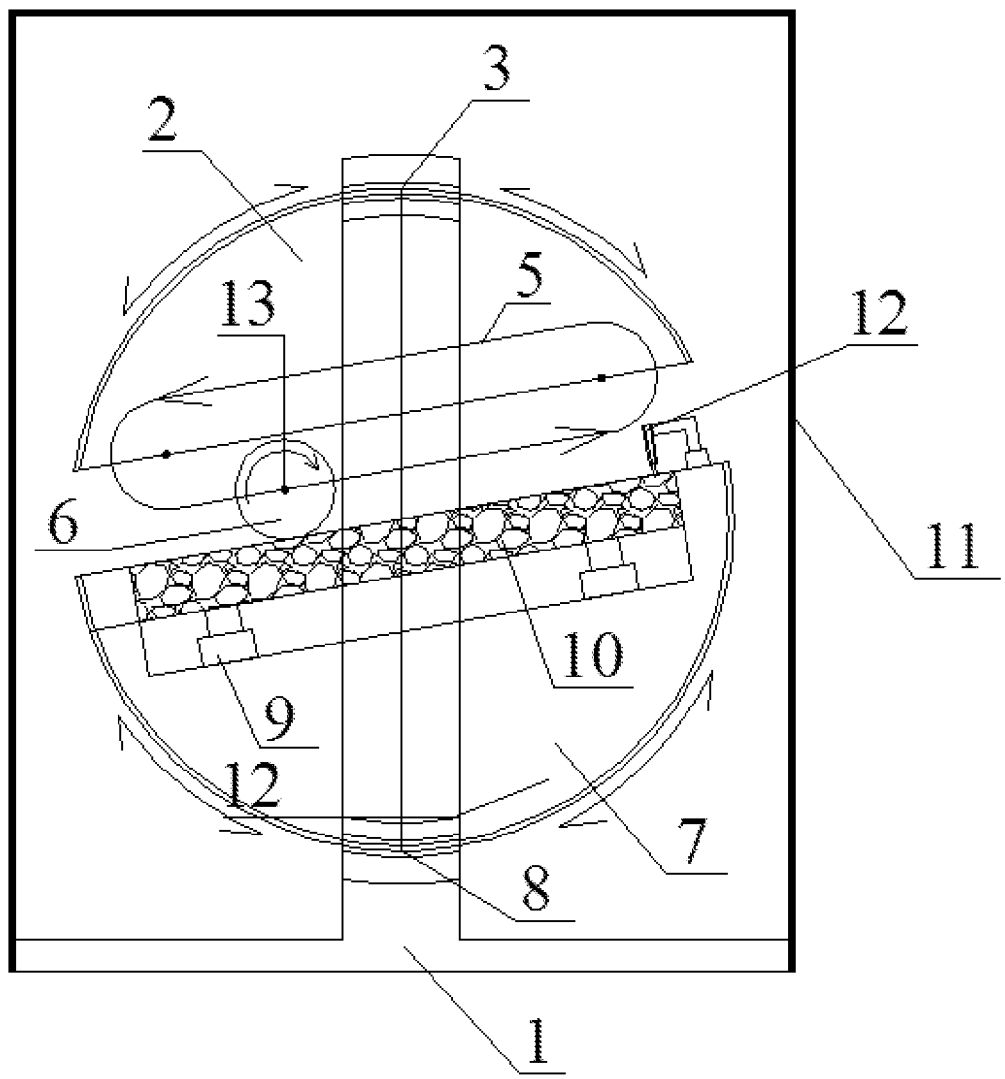
FIG. 3 is a front view of a slope one-way loading rutting test device according to some embodiments of the present disclosure when simulating slope loading.
Figure 4:
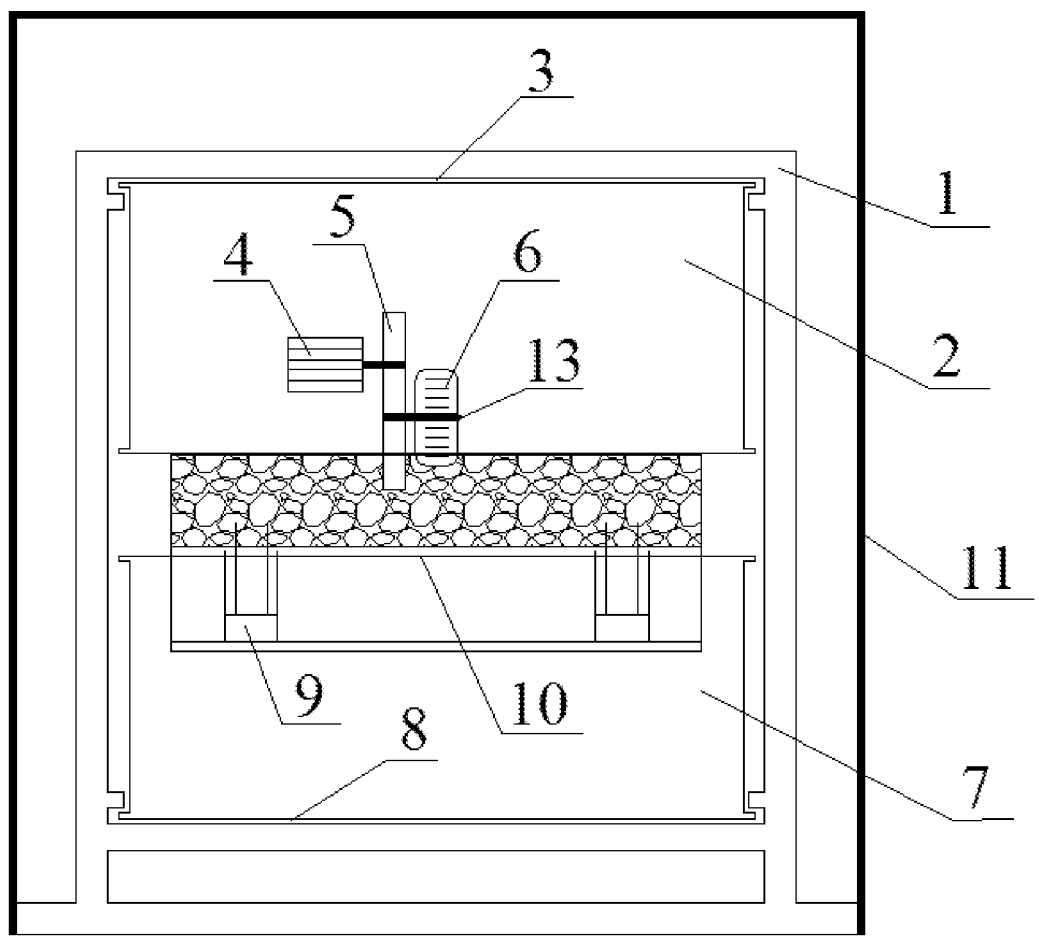
FIG. 4 is a side view of a slope one-way loading rutting test device according to some embodiments of the present disclosure when simulating slope loading.

As shown in FIG. 1 to FIG. 4, a slope one-way loading rutting test device in this embodiment comprises a frame 1, a loading frame rotating assembly 3, a loading frame 2, a variable speed motor 4, a runner wheel 6, a bearing frame 7, a bearing frame rotating assembly 8, a height adjusting device 9, a test piece mounting frame 10 and a temperature control box 11, wherein the upper part of the loading frame 2 is slidably connected with an upper cross beam of the frame 1 through the loading frame rotating assembly 3, and the variable speed motor 4 and the runner wheel 6 are embedded in the lower part of the loading frame 2; the variable speed motor 4 is in transmission connection with the runner wheel 6 to realize one-way continuous loading of the runner wheel 4 on a test piece; the lower part of a bearing frame 7 is slidably connected with a lower cross beam of the frame 1 through a bearing frame rotating assembly 8, and the test piece mounting frame 10 and the height adjusting device 9 are sequentially embedded into the upper part of the bearing frame 7 from top to bottom; the height of the test piece mounting frame 10 is adjusted through the height adjusting device 9; the temperature control box 11 wraps the frame 1 in a closed mode and is used for regulating and controlling the test environment temperature.

The technical effects achieved by this embodiment are as follows. This embodiment solves the problems that a rutting tester in the prior art cannot simulate rutting damage on road surfaces of different slopes under different traffic flows when considering the uphill and downhill of vehicles, and simulation cannot truly reflect the actual effect of wheels on the road surface of a traffic lane. The structure is simple, the processing cost is obviously reduced, and the experimental results are good.

Embodiment 2

As shown in FIG. 1 to FIG. 4, a slope one-way loading rutting test device in this embodiment comprises all the technical features in embodiment 1. In addition, the device further comprises a transmission chain 5, one end of the transmission chain 5 is connected with the variable speed motor 4, the other end of the transmission chain 5 is connected with the rotating mandrel of the runner wheel 6, the transmission chain 5 serves as a transmission device for the variable speed motor 4 driving the runner wheel 6 to run and load, and the runner wheel 6 is a pneumatic rubber tire.

Specifically, the rotating spindle of the variable speed motor 4 is in transmission connection with the transmission chain 5, the variable speed motor 4 drives the runner wheel 6 to run and load through the transmission chain 5 with adjustable rotating speed, and the variable speed motor 4 is fixedly mounted on the bottom of the loading frame 2.

The embodiment has the beneficial effect that the transmission chain 5 is used for transmission, so that the transmission is stable, the slip phenomenon does not occur, and the operation is stable. The variable speed motor 4 realizes speed adjustment.

Embodiment 3

As shown in FIG. 1 to FIG. 4, a slope one-way loading rutting test device in this embodiment comprises all the technical features in embodiment 2. In addition, the device further comprises a temperature sensor 12 and a displacement sensor 13, wherein the temperature sensor 12 is used to measure the surface temperature of the test piece in the experimental process, and the displacement sensor 13 is used to measure the vertical displacement of the surface of the test piece which changes with time under the action of the runner wheel 6 in the experimental process.

For example, the temperature sensor 12 is provided on the bearing frame 7, and the displacement sensor 13 is provided at the rotating mandrel of the runner wheel 6, which can detect the displacement when the runner wheel 6 moves between the loading frame 2 and the bearing frame 7.

The embodiment has the beneficial effect that the temperature sensor 12 and the displacement sensor 13 are provided, so that an excellent detection feedback effect is achieved, and the intelligent degree is remarkably improved.

Embodiment 4

As shown in FIG. 1 to FIG. 4, a slope one-way loading rutting test device in this embodiment comprises all the technical features in embodiment 2. In addition, the frame 1 has a rectangular door frame structure, the frame 1 consists of left and right upright posts and upper and lower cross beams, and the frame 1 mainly provides a stable working platform for test loading.

Preferably, the loading frame rotating assembly 3 consists of upper and lower arc sliding plates, the shapes of the upper and lower arc sliding plates are semi-circular, the inner diameter of the semi-circular sliding plates is equal to the outer diameter of the semi-circular arc of the loading frame 2, and the two arcs are concentric.

Preferably, the shape of the loading frame 2 is semi-cylindrical, and the loading frame rotating assembly 3 is mounted on the top of the semi-circular arc of the loading frame 2.

Preferably, the shape of the bearing frame 7 is semi-cylindrical, the bearing frame 7 has the same radius and height as the semi-cylinder of the loading frame 2, the bearing frame rotating assembly 8 is mounted on the top of the semi-circular arc of the bearing frame 7, and the mounting height of the bearing frame 7 ensures that the semi-circular arc center of the loading frame 2 coincides with the semi-circular arc center of the bearing frame 7, so as to ensure that the opposite faces of the loading frame 2 and the bearing frame 7 are always parallel faces when the loading frame 2 and the bearing frame 7 rotate at the same angle in the same direction.

Preferably, the bearing frame rotating assembly 8 consists of upper and lower arc sliding plates, the shapes of the upper and lower arc sliding plates are semi-circular, the inner diameter of the semi-circular sliding plates is equal to the outer diameter of the semi-circular arc of the bearing frame 7, and the two arcs are concentric.

The embodiment has the beneficial effect that the structure is simple, the stability is obviously improved, and the operation is stable.

Embodiment 5

As shown in FIG. 1 to FIG. 4, a slope one-way loading rutting test device in this embodiment comprises all the technical features in embodiment 2. In addition, the height adjusting device 9 is a hydraulic height adjusting system, the height adjusting device 9 adjusts the contact pressure of the runner wheel 6 by adjusting the height of the test piece mounting frame 10, the height adjusting device 9 is mounted between the test piece mounting frame 10 and the bearing frame 7, the upper end of the height adjusting device 9 is fixedly connected with the test piece mounting frame 10, and the lower end of the height adjusting device 9 is fixedly connected with the bearing frame 7; the test piece mounting frame 10 is a rectangular steel platform, the upper surface of the test piece mounting frame 10 is provided with a test mold neck which plays a role of fixing a test mold, and the lower surface of the test piece mounting frame 10 is seated and fixedly mounted right above the height adjusting device 9; the temperature control box 11 has a rectangular box structure, and the temperature control box 11 has the functions of heating up and preserving heat, and is used for regulating and controlling the temperature of the test environment.

Compared with the traditional asphalt mixture rutting tester, the slope one-way loading rutting tester provided by the present disclosure has the following beneficial effects. On the one hand, in terms of the test piece loading mode, the runner wheel 6 adopts a pneumatic rubber wheel for one-way continuous loading, and the running speed and the contact pressure of the runner wheel 6 are adjustable, which changes the fact that the existing rutting tester adopts solid rubber runner wheels 6 for reciprocating cyclic loading and cannot truly simulate the actual effect of wheels on the road surface of a traffic lane. On the other hand, in the mounting position of the test piece, the oblique arrangement is adopted, and the inclination angle is adjustable, which changes the situation that the existing rutting tester can only load the test piece horizontally, but cannot simulate the rutting damage on road surfaces of different slopes when considering the uphill and downhill of vehicles. On the whole, the slope one-way loading rutting test device can simulate the rutting damage on road surfaces of different slopes under different traffic flows when considering the uphill and downhill of vehicles, and the runner wheel 6 adopts a pneumatic rubber wheel for one-way continuous loading, which is closer to the actual effect of wheels on the road surface of a traffic lane. In the design, considering the actual effect of the real wheels on the road surface of a traffic lane and the prevailing reality of the longitudinal slope of the road surface, the test piece is obliquely arranged with the angle is adjustable, the runner wheel 6 adopts an pneumatic rubber wheel for one-way continuous loading, and the running speed and the contact pressure of the runner wheel 6 are adjustable, so that the problems that an existing rutting tester cannot simulate rutting damage on road surfaces of different slopes under different traffic flows when considering the uphill and downhill of vehicles, and simulation cannot truly reflect the actual effect of wheels on the road surface of a traffic lane are effectively solved.

Although the present disclosure has been described in detail with general descriptions and specific embodiments, it is obvious to those skilled in the art that some modifications or improvements can be made on the basis of the present disclosure. Therefore, these modifications or improvements made on the basis of not deviating from the spirit of the present disclosure belong to the scope of protection of the present disclosure.

Words such as "upper", "lower", "left", "right" and "middle" used in this specification are only for convenience of description and clarity, rather than limit the implementable scope of the present disclosure. The change or adjustment of their relative relationship shall be regarded as the implementable scope of the present disclosure without substantial change of technical content.

What is claimed is:

1. A slope one-way loading rutting test device, comprising: a frame having an upper cross beam and lower cross beam, a loading frame rotating assembly consisting of upper and lower arc sliding plates forming an arc with an inner diameter, and the upper and lower arc sliding plates being semi-circular; a loading frame having a top, a bottom, an upper part, a lower part, a radius, and a height, the loading frame being semi-cylindrical and forming an arc with a top, a center, and an outer diameter that is equal to the inner diameter of the semi-circular sliding plates of the loading frame rotating assembly, the arc of the loading frame rotating assembly and the arc of the loading frame being concentric; a variable speed motor in transmission connection with a runner wheel to realize one-way continuous loading of the runner wheel on a test piece, a bearing frame; having an upper part, a lower part, a radius, and a height, the bearing frame being semi-cylindrical, forming an arc with a center, and having the same radius and height as the semi-cylinder of the loading frame; a bearing frame rotating assembly consisting of upper and lower arc sliding plates that are semi- circular and form an arc with an inner diameter that is equal to the outer diameter of the arc of the loading frame, the arc of the bearing frame rotating assembly and the arc of the bearing frame being concentric, and the bearing frame and the loading frame having opposing faces; a test piece mounting frame having a height that is adjusted by a height adjusting device and a temperature control box wrapping the frame in a closed mode and is used for regulating and controlling the test environment temperature; wherein, the upper part of the loading frame is slidably connected with the upper cross beam of the frame through the loading frame rotating assembly; the variable speed motor and the runner wheel are embedded in the lower part of the loading frame; the lower part of the bearing frame is slidably connected with the lower cross beam of the frame through the bearing frame rotating assembly; the test piece mounting frame and the height adjusting device are sequentially embedded into the upper part of the bearing frame from top to bottom; the loading frame rotating assembly is mounted on the top of the semi-circular arc of the loading frame, the bearing frame rotating assembly is mounted on the top of the arc of the bearing frame at a mounting height, the mounting height of the bearing frame ensuring that the arc of the loading frame coincides with the center of the arc center of the bearing frame, and the opposite faces of the loading frame and the bearing frame are parallel when the loading frame and the bearing frame rotate.

2. The slope one-way loading rutting test device according to claim 1, further comprising a transmission chain having one end and another end, where the one end of the transmission chain is connected with the variable speed motor, and the other end of the transmission chain is connected with the runner wheel, the transmission chain serving as a transmission device for the variable speed motor driving the runner wheel to run and load the test piece, and the runner wheel is a pneumatic rubber tire.

3. The slope one-way loading rutting test device according to claim 2; wherein,
- the variable speed motor has a rotating spindle in transmission connection with the transmission chain;
- the variable speed motor drives the runner wheel to run and load through the transmission chain with an adjustable rotating speed; and,
- the variable speed motor is fixedly mounted on the bottom of the loading frame.

4. The slope one-way loading rutting test device according to claim 1, further comprising a temperature sensor and a displacement sensor; wherein,
- the temperature sensor is used to measure a surface temperature of the test piece in an experimental process; and,
- the displacement sensor is used to measure a vertical displacement of the surface of the test piece which changes with time under an action of the runner wheel in the experimental process.

5. The slope one-way loading rutting test device according to claim 1; wherein,
- the frame has a rectangular door frame structure;
- the frame consists of left and right upright posts and upper and lower cross beams; and,
- the frame mainly provides a stable working platform for test loading.

6. The slope one-way loading rutting test device according to claim 1, wherein
- the height adjusting device is a hydraulic height adjusting system;
- the height adjusting device adjusts the contact pressure of the runner wheel by adjusting the test piece mounting frame to a height;
- the height adjusting device is mounted between the test piece mounting frame and the bearing frame, the upper end of the height adjusting device is fixedly connected with the test piece mounting frame, and the lower end of the height adjusting device is fixedly connected with the bearing frame;
- the test piece mounting frame is a rectangular steel platform, the upper surface of the test piece mounting frame is provided with a test mold neck which plays a role of fixing a test mold, and the lower surface of the test piece mounting frame is seated and fixedly mounted right above the height adjusting device; and,
- the temperature control box has a rectangular box structure and functions to heat and preserve heat in the test environment, and regulating and controlling the temperature of the test environment.

* * * * *